United States Patent
Rangaiah et al.

(10) Patent No.: US 7,744,600 B2
(45) Date of Patent: Jun. 29, 2010

(54) BONE RESECTION GUIDE AND METHOD

(75) Inventors: Chetan Rangaiah, Warsaw, IN (US);
Prashanth Hegde, Warsaw, IN (US);
Maleata Y. Hall, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 882 days.

(21) Appl. No.: 11/329,315

(22) Filed: Jan. 10, 2006

(65) Prior Publication Data
US 2007/0173850 A1 Jul. 26, 2007

(51) Int. Cl.
*A61B 17/58* (2006.01)
(52) U.S. Cl. .................................................... 606/88
(58) Field of Classification Search ............ 606/87–89, 606/86 R
See application file for complete search history.

(56) References Cited

U.S. PATENT DOCUMENTS

| | | | |
|---|---|---|---|
| 4,211,228 A | 7/1980 | Cloutier | |
| 4,421,112 A | 12/1983 | Mains et al. | |
| 4,457,307 A | 7/1984 | Stillwell | |
| 4,467,801 A | 8/1984 | Whiteside | |
| 4,487,203 A | 12/1984 | Androphy | |
| 4,493,317 A | 1/1985 | Klaue | 606/69 |
| 4,501,266 A | 2/1985 | McDaniel | |
| 4,524,766 A | 6/1985 | Petersen | 606/88 |
| 4,566,448 A | 1/1986 | Rohr, Jr. | |
| 4,567,886 A | 2/1986 | Petersen | |
| 4,653,488 A | 3/1987 | Kenna | |
| 4,736,737 A | 4/1988 | Fargie et al. | |
| 4,759,350 A | 7/1988 | Dunn et al. | 606/82 |
| 4,841,975 A | 6/1989 | Woolson | 600/425 |
| 4,892,093 A | 1/1990 | Zarnowski et al. | |
| 4,907,577 A | 3/1990 | Wu | 606/87 |

(Continued)

FOREIGN PATENT DOCUMENTS

EP 0538152 8/1995

(Continued)

OTHER PUBLICATIONS

Nexgen Complete Knee Solution, Intramedullary Instrumentation Surgical Technique, For The NexGen Cruciate Retaining & Legacy Posterior Stabilized Knee, Zimmer, Inc. 97-5973-102 Rev. 1 (1998).

(Continued)

*Primary Examiner*—Eduardo C Robert
*Assistant Examiner*—Ellen C Hammond
(74) *Attorney, Agent, or Firm*—Baker & Daniels LLP

(57) ABSTRACT

An apparatus is provided for guiding a cutter to cut a bone to receive a knee prosthesis and methods for its use. In one aspect of the invention a relative angle adjustment mechanism is provided to adjust the relative angle between first and second cut guides. In another aspect of the invention, a cut guide is hinged to a mounting base such that it is rotatable about the hinge between a first position in which the cut guide is adjacent to the bone and a second position in which the cut guide is spaced from the bone. In another aspect of the invention, a mounting base includes an initial fixation mechanism and a secondary fixation mechanism.

16 Claims, 6 Drawing Sheets

U.S. PATENT DOCUMENTS

| | | | |
|---|---|---|---|
| 4,913,137 A | 4/1990 | Azer et al. | |
| 4,952,213 A | 8/1990 | Bowman et al. | |
| 5,002,545 A | 3/1991 | Whiteside et al. | |
| 5,002,547 A | 3/1991 | Poggie et al. | 606/88 |
| 5,007,936 A | 4/1991 | Woolson | 128/898 |
| 5,037,423 A | 8/1991 | Kenna | |
| 5,053,037 A | 10/1991 | Lackey | |
| 5,062,722 A | 11/1991 | Shiozaki et al. | |
| 5,092,037 A | 3/1992 | Pinkerton | |
| 5,100,408 A | 3/1992 | Lackey | |
| 5,116,338 A | 5/1992 | Poggie et al. | 606/90 |
| 5,154,717 A | 10/1992 | Matsen, III et al. | 606/53 |
| 5,171,277 A | 12/1992 | Roger | 606/86 |
| 5,209,750 A | 5/1993 | Stef | |
| 5,230,338 A | 7/1993 | Allen et al. | 600/429 |
| 5,234,433 A | 8/1993 | Bert et al. | |
| 5,251,127 A | 10/1993 | Raab | 606/130 |
| 5,275,603 A | 1/1994 | Ferrante et al. | |
| 5,282,803 A | 2/1994 | Lackey | |
| 5,305,203 A | 4/1994 | Raab | 606/1 |
| 5,342,367 A | 8/1994 | Ferrante et al. | |
| 5,342,368 A * | 8/1994 | Petersen | 606/88 |
| 5,364,401 A | 11/1994 | Ferrante et al. | |
| 5,364,402 A | 11/1994 | Mumme et al. | |
| 5,411,505 A | 5/1995 | Mumme | |
| 5,413,579 A | 5/1995 | Du Toit | 606/87 |
| 5,417,694 A | 5/1995 | Marik et al. | |
| 5,431,653 A | 7/1995 | Callaway | |
| 5,431,656 A | 7/1995 | Clift, Jr. et al. | |
| 5,445,642 A | 8/1995 | McNulty et al. | |
| 5,454,816 A | 10/1995 | Ashby | |
| 5,470,335 A | 11/1995 | Du Toit | 606/73 |
| 5,474,559 A | 12/1995 | Bertin et al. | 606/89 |
| 5,484,446 A | 1/1996 | Burke et al. | 606/87 |
| 5,486,178 A | 1/1996 | Hodge | |
| 5,486,180 A | 1/1996 | Dietz et al. | 606/87 |
| 5,514,139 A | 5/1996 | Goldstein et al. | |
| 5,514,140 A | 5/1996 | Lackey | |
| 5,551,429 A | 9/1996 | Fitzpatrick et al. | 600/426 |
| 5,562,674 A | 10/1996 | Stalcup et al. | 606/88 |
| 5,569,261 A | 10/1996 | Marik et al. | |
| 5,584,838 A | 12/1996 | Rona et al. | 606/96 |
| 5,593,411 A | 1/1997 | Stalcup et al. | 606/88 |
| 5,597,379 A | 1/1997 | Haines et al. | |
| 5,611,802 A | 3/1997 | Samuelson et al. | |
| 5,628,750 A | 5/1997 | Whitlock et al. | |
| 5,634,929 A | 6/1997 | Misko et al. | 606/130 |
| 5,643,272 A | 7/1997 | Haines et al. | |
| 5,649,928 A | 7/1997 | Grundei | |
| 5,669,914 A | 9/1997 | Eckhoff | |
| 5,676,668 A | 10/1997 | McCue et al. | |
| 5,681,316 A * | 10/1997 | DeOrio et al. | 606/88 |
| 5,682,886 A | 11/1997 | Delp et al. | 600/407 |
| 5,683,397 A | 11/1997 | Vendrely et al. | |
| 5,683,398 A | 11/1997 | Carls et al. | |
| 5,720,752 A | 2/1998 | Elliott et al. | |
| 5,743,915 A | 4/1998 | Bertin et al. | 606/88 |
| 5,743,916 A | 4/1998 | Greenberg et al. | 606/102 |
| 5,748,767 A | 5/1998 | Raab | 382/128 |
| 5,788,700 A | 8/1998 | Morawa et al. | |
| 5,810,831 A | 9/1998 | D'Antonio | |
| 5,834,759 A | 11/1998 | Glossop | 250/203.1 |
| 5,871,018 A | 2/1999 | Delp et al. | 128/898 |
| 5,888,034 A | 3/1999 | Greenberg | 408/115 R |
| 5,891,158 A | 4/1999 | Manwaring et al. | 606/130 |
| 5,904,691 A | 5/1999 | Barnett et al. | 606/130 |
| 5,911,723 A | 6/1999 | Ashby et al. | |
| 5,921,992 A | 7/1999 | Costales | 606/130 |
| 5,995,738 A | 11/1999 | DiGioia, III et al. | 703/11 |
| 6,002,859 A | 12/1999 | DiGioia, III et al. | 703/11 |
| 6,022,377 A | 2/2000 | Nuelle et al. | |
| 6,033,415 A | 3/2000 | Mittelstadt et al. | 606/130 |
| 6,056,756 A | 5/2000 | Eng et al. | |
| 6,074,394 A | 6/2000 | Krause | 606/86 |
| 6,077,270 A | 6/2000 | Katz | |
| 6,081,741 A | 6/2000 | Hollis | 600/424 |
| 6,090,114 A | 7/2000 | Matsuno et al. | |
| 6,096,043 A | 8/2000 | Techiera et al. | |
| 6,096,082 A | 8/2000 | Stegmuller et al. | |
| 6,106,529 A | 8/2000 | Techiera | |
| 6,162,228 A | 12/2000 | Durham | 606/96 |
| 6,167,145 A | 12/2000 | Foley et al. | 382/128 |
| 6,234,429 B1 | 5/2001 | Yang | |
| 6,267,762 B1 | 7/2001 | Millard et al. | |
| 6,267,770 B1 | 7/2001 | Truwit | 606/130 |
| 6,285,902 B1 | 9/2001 | Kienzle, III et al. | 600/427 |
| 6,338,716 B1 | 1/2002 | Hossack et al. | 600/459 |
| 6,342,056 B1 | 1/2002 | Mac-Thiong | 606/96 |
| 6,396,939 B1 | 5/2002 | Hu et al. | 382/128 |
| 6,402,762 B2 | 6/2002 | Hunter | 606/130 |
| 6,430,434 B1 | 8/2002 | Mittelstadt | 600/426 |
| 6,450,978 B1 | 9/2002 | Brosseau | 600/595 |
| 6,458,135 B1 | 10/2002 | Harwin et al. | |
| 6,477,400 B1 | 11/2002 | Barrick | 600/426 |
| 6,490,467 B1 | 12/2002 | Bucholz | 600/407 |
| 6,490,475 B1 | 12/2002 | Seeley | 600/426 |
| 6,503,249 B1 | 1/2003 | Krause | 606/62 |
| 6,514,259 B2 | 2/2003 | Picad et al. | |
| 6,533,790 B1 | 3/2003 | Liu | 606/73 |
| 6,551,325 B2 | 4/2003 | Neubauer et al. | |
| 6,554,837 B1 | 4/2003 | Hauri et al. | |
| 6,575,980 B1 | 6/2003 | Robie et al. | |
| 6,595,997 B2 | 7/2003 | Axelson, Jr. et al. | |
| 6,638,281 B2 | 10/2003 | Gorek | 606/96 |
| 6,648,896 B2 | 11/2003 | Overes et al. | |
| 6,685,711 B2 | 2/2004 | Axelson, Jr. et al. | |
| 6,695,848 B2 | 2/2004 | Haines | |
| 6,712,824 B2 | 3/2004 | Millard et al. | |
| 6,740,092 B2 | 5/2004 | Lombardo et al. | |
| 6,758,850 B2 | 7/2004 | Smith et al. | |
| 6,796,986 B2 | 9/2004 | Duffner | |
| 6,852,115 B2 * | 2/2005 | Kinnett | 606/88 |
| 6,859,661 B2 | 2/2005 | Tuke | |
| 6,920,347 B2 | 7/2005 | Simon et al. | |
| 6,932,823 B2 | 8/2005 | Grimm et al. | |
| 6,942,700 B2 | 9/2005 | Williamson | |
| 6,962,593 B2 | 11/2005 | Sanford et al. | |
| 7,029,477 B2 * | 4/2006 | Grimm | 606/88 |
| 7,033,361 B2 * | 4/2006 | Collazo | 606/87 |
| 7,241,298 B2 | 7/2007 | Nemec et al. | |
| 7,309,339 B2 | 12/2007 | Cusick et al. | |
| 7,335,206 B2 * | 2/2008 | Steffensmeier et al. | 606/88 |
| 2002/0133160 A1 | 9/2002 | Axelson, Jr. et al. | |
| 2002/0133162 A1 | 9/2002 | Axelson, Jr. et al. | |
| 2002/0151894 A1 | 10/2002 | Melkent | 606/61 |
| 2002/0165552 A1 | 11/2002 | Duffner | |
| 2003/0069585 A1 | 4/2003 | Axelson, Jr. et al. | |
| 2003/0069591 A1 | 4/2003 | Carson et al. | |
| 2003/0083667 A1 | 5/2003 | Ralph | 606/96 |
| 2003/0171757 A1 | 9/2003 | Coon et al. | |
| 2003/0181919 A1 | 9/2003 | Gorek | 606/96 |
| 2003/0187351 A1 | 10/2003 | Franck | |
| 2003/0212403 A1 | 11/2003 | Swanson | |
| 2004/0039396 A1 | 2/2004 | Couture et al. | |
| 2004/0073228 A1 | 4/2004 | Kienzle | 606/96 |
| 2004/0122305 A1 | 6/2004 | Grimm | 600/407 |
| 2004/0153066 A1 | 8/2004 | Coon et al. | |
| 2004/0153083 A1 | 8/2004 | Nemec et al. | |
| 2004/0172044 A1 * | 9/2004 | Grimm et al. | 606/130 |
| 2005/0021039 A1 | 1/2005 | Cusick et al. | |
| 2005/0049603 A1 | 3/2005 | Calton et al. | |
| 2005/0055028 A1 | 3/2005 | Haines | |
| 2005/0070910 A1 | 3/2005 | Keene | |
| 2005/0149039 A1 | 7/2005 | Haines et al. | |

| | | | |
|---|---|---|---|
| 2005/0149040 A1 | 7/2005 | Haines | |
| 2005/0149041 A1 | 7/2005 | McGinley et al. | |
| 2005/0171545 A1 | 8/2005 | Walsh et al. | |
| 2005/0182415 A1 | 8/2005 | Steffensmeier et al. | |
| 2005/0187557 A1 | 8/2005 | Collazo | |
| 2005/0203528 A1 | 9/2005 | Couture et al. | |
| 2005/0209598 A1 | 9/2005 | Grimm | |
| 2005/0228393 A1 | 10/2005 | Williams et al. | |
| 2005/0234454 A1 | 10/2005 | Chin | |
| 2005/0234465 A1 | 10/2005 | McCombs | |
| 2005/0234466 A1 | 10/2005 | Stallings | |
| 2005/0273113 A1 | 12/2005 | Kuczynski | |
| 2005/0273114 A1 | 12/2005 | Novak | |
| 2006/0149276 A1 * | 7/2006 | Grimm | 606/88 |
| 2007/0149977 A1 * | 6/2007 | Heavener | 606/87 |
| 2007/0173849 A1 | 7/2007 | Claypool et al. | |

FOREIGN PATENT DOCUMENTS

| | | |
|---|---|---|
| EP | 0384562 | 7/1996 |
| EP | 0556998 | 6/1997 |
| EP | 0839501 | 7/1998 |
| EP | 0720834 | 6/1999 |
| EP | 1323386 | 7/2003 |
| EP | 1424042 | 2/2004 |
| EP | 1430842 | 6/2004 |
| EP | 1442712 | 8/2004 |
| EP | 0778751 | 5/2005 |
| EP | 1574177 | 9/2005 |
| EP | 1579812 | 9/2005 |
| JP | 11244315 | 9/1999 |
| WO | WO 96/07361 | 3/1996 |
| WO | WO 9629940 | 10/1996 |
| WO | WO 9629940 A1 * | 10/1996 |

OTHER PUBLICATIONS

Nexgen Complete Knee Solution, Posterior Reference, Multi-Referenced 4-in-1 Femoral Instrumentation; Posterior Reference Surgical Technique, For NexGen Cruciate Retaining & Legacy Posterior Stabilized Knees, Zimmer, Inc. 97-5973-402 Rev1 (1998).

Nexgen Complete Knee Solution, Micro-Mill Instrumentation Surgical Technique, For The NexGen Cruciate Retaining & Legacy Posterior Stabilized Knee, Zimmer, Inc. 97-5970-103 (1998).

Nexgen Complete Knee Solution, Revision Instrumentation Surgical Technique for Legacy Knee Constrained Condylar Knee, Zimmer, Inc. 97-5994-202 (2001).

Revision Knee Arthroplasty Surgical Guidelines, $2^{nd}$ Edition, by Kelly Vince, M.D., John Insall, M.D., Robert Booth, Jr., M.D. and Giles Scuderi, M.D., Zimmer, Inc. 97-5224-03 Rev. 1 (1999).

U.S. Appl. No. 10/795,830, filed Mar. 8, 2004, Grimm.

U.S. Appl. No. 10/795,621, filed Mar. 8, 2004, Grimm.

U.S. Appl. No. 10/979,734, filed Nov. 2, 2004, Grimm.

U.S. Appl. No. 11/287,839, filed Nov. 28, 2005, Heavener.

Nexgen Complete Knee Solution, The Zimmer Institute Surgical Technique MIS Quad-Sparing Surgical Technique for Total Knee Arthroplasty, 2004.

* cited by examiner

BONE RESECTION GUIDE AND METHOD

FIELD OF THE INVENTION

The invention relates to a bone resection apparatus and method for guiding a cutter to cut a bone to receive a knee prosthesis.

BACKGROUND

Degenerative and traumatic damage to the articular cartilage of the knee joint can result in pain and restricted motion. Knee replacement surgery is frequently utilized to alleviate the pain and restore joint function. An incision is made into the knee joint to expose the joint. Cutting guides are used to guide the removal of the articular surfaces that are to be replaced. Artificial joint components are positioned to replace the resected bone ends in order to establish the desired alignment and mechanics of the joint. In a total knee replacement, all of the articulating compartments of the joint are repaired with prosthetic components. However, often only one compartment of the knee joint, typically the medial compartment, is impaired. Thus, in a unicondylar knee replacement, only the damaged compartment is repaired with prosthetic bearing components.

FIGS. 1-3 illustrate several aspects of implant orientation. FIG. 1 illustrates various axes of the lower limb in the frontal plane. Axes can be defined for each segment of the lower limb. For example, the femur 1 has an anatomic axis 2 coinciding generally with its intramedullary canal. It also has a mechanical axis 4, or load axis, running from the center of the femoral head to the center of the knee. The angle 6 between these two axes 2, 4 in the frontal plane varies within the patient population but is on the order of 4-9°. The two axes 2, 4 are approximately superimposed in the sagittal plane (FIG. 2). Likewise, the tibia 3 has a mechanical axis 5 coinciding generally with its intramedullary canal. The mechanical axis 5 of the tibia runs from the center of the knee to the center of the ankle. The transverse axis, or joint line 8, about which the knee flexes, is parallel to a line through the medial and lateral femoral condyles and parallel to the tibial plateau. Typically, the distal femur and proximal tibia are resected to be parallel to the joint line 8, and thus perpendicular to the mechanical axes 4, 5 as indicated at 10 and 12. The intersection of the femoral and tibial mechanical axes 4, 5 may subtend a small angle relative to one another. However, the angle is small such that the axes 4,5 are approximately collinear and may be treated as collinear for most purposes.

FIG. 2 illustrates the knee joint from the side or sagittal view and various bone cuts that may be made to align implant components. The distal femoral cut 10 is typically made perpendicular to the femoral axes 2, 4 in the sagittal plane. The proximal tibial resection 12 is typically cut to match the natural posterior slope, or rotation, 16 of the proximal tibia relative to the mechanical axes 4, 5. The amount of posterior slope 16 relative to a reference line 18 perpendicular to the mechanical axes 4, 5 varies in the patient population but is on the order of 7°. The distance between the distal femoral cut 10 and proximal tibial cut 12 along the mechanical axes 4, 5 is the extension gap. Other cuts may be made depending on the components that are to be implanted. These include an anterior femoral cut 20, anterior femoral chamfer cut 22, posterior femoral chamfer cut 24, and posterior femoral cut 26. The patella 7 may also be cut 28 to allow for replacement of the patellar articular surface. In a unicondylar knee replacement, only the medial or lateral side of the knee joint is resurfaced. Furthermore, the trochlear, or patellar bearing, surface of the femur is typically left intact in a unicondylar procedure. Unicondylar implant designs vary, but typically only the distal femoral cut 10, posterior femoral chamfer cut 24, and posterior femoral cut 26 are needed to accommodate the unicondylar femoral implant.

FIG. 3 depicts six aspects of component positioning relative to a coordinate system in which the x-axis 30 corresponds approximately to the joint line 8, the z-axis 34 corresponds approximately to the mechanical axes 4 and 5, and the y-axis 32 is normal to the other two. Position along each of these axes is depicted by arrows. Position along the x, y, and z axes determines the medial/lateral (dx) 36, anterior/posterior (dy) 38, and proximal/distal (dz) 40 positioning of components respectively. Rotation about each of these axes is also depicted by arrows. Rotation about the z-axis (rz) 42 corresponds anatomically to external rotation of the femoral component, rotation about the x-axis (rx) 44 corresponds to extension plane rotation, and rotation about the y-axis (ry) 46 corresponds to varus/valgus rotation.

Many surgical procedures are now performed with surgical navigation systems in which sensors detect tracking elements attached in known relationship to an object in the surgical suite such as a surgical instrument, implant, or patient body part. The sensor information is fed to a computer that then triangulates the three dimensional position of the tracking elements within the surgical navigation system coordinate system. Thus, the computer can resolve the position and orientation of the object and provide position and orientation feedback for surgeon guidance. For example, the position and orientation can be shown superimposed on an image of the patient's anatomy obtained via X-ray, CT scan, ultrasound, or other imaging technology.

SUMMARY

The present invention provides an apparatus for guiding a cutter to cut a bone to receive a knee prosthesis and methods for its use.

In one aspect of the invention, the apparatus includes a first cut guide and a second cut guide mounted to the first cut guide. A relative angle adjustment mechanism is connected between the first and second cut guides to adjust the relative angle between a cut plane defined by the first cut guide and a cut plane defined by the second cut guide.

In another aspect of the invention, the apparatus includes a mounting base and a cut guide defining a cut plane. The cut guide is hinged to the mounting base such that it is rotatable about the hinge between a first position in which the cut guide is adjacent to the bone and a second position in which the cut guide is spaced from the bone.

In another aspect of the invention the apparatus includes a mounting base and a cut guide mounted to the mounting base. The mounting base includes an initial fixation mechanism and a secondary fixation mechanism. The initial fixation mechanism is operable to rotate the mounting base relative to the bone to vary the extension plane angle of the cut guide and the secondary fixation mechanism is operable to secure the mounting base in fixed relationship to the bone to fix the extension plane angle.

In another aspect of the invention a method includes positioning a cut guide assembly adjacent to the knee joint, the cut guide assembly defining tibial and femoral cut planes; operating an extension plane adjustment mechanism to adjust the relative extension plane angle between the tibial and femoral cut planes to a desired relative extension plane angle; guiding a cutter with the tibial cut guide to cut the tibia in the tibial cut plane; and guiding a cutter with the femoral cut guide to cut the femur in the femoral cut plane.

In another aspect of the invention a method includes securing a bone resection apparatus to the bone; rotating the cut guide about a hinge between a first position in which the cut guide is spaced from the bone and a second position in which the cut guide is adjacent the bone; and guiding a cutter with the cut guide to cut the bone in the cut plane.

In another aspect of the invention a method includes securing a bone resection apparatus to the bone; rotating a mounting base about an axis of a first fixation mechanism to vary the extension plane angle of a cut plane; operating a second fixation mechanism to secure the mounting base in fixed relationship to the bone to fix the extension plane angle of the cut plane; and guiding a cutter with the cut guide to cut the bone in the cut plane.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 3:
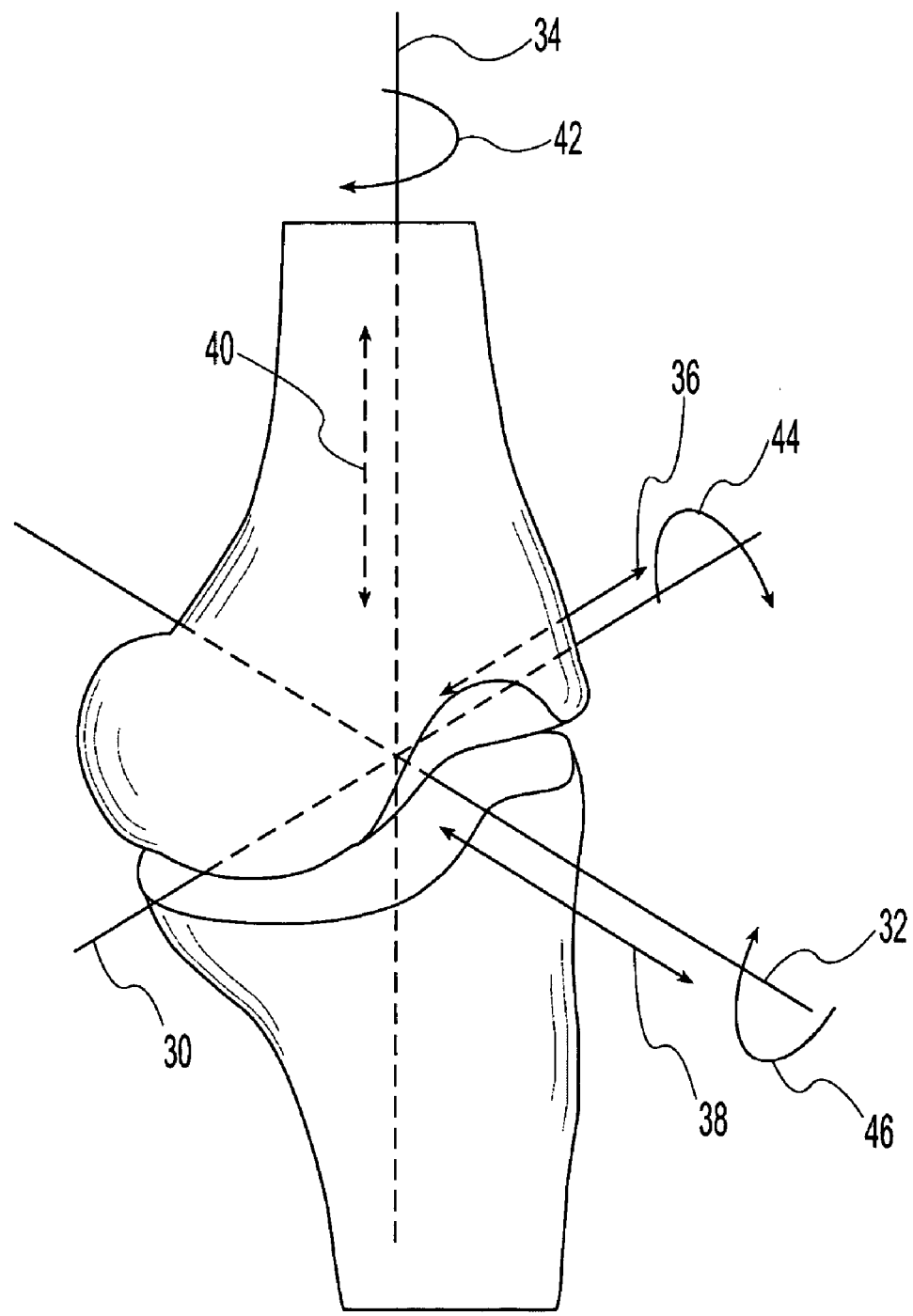
FIG. 3 is a perspective view of knee joint showing aspects of component positioning.

Embodiments of a bone resection guide include a first cut guide having a cutter guide defining a first cut plane and able to guide a saw blade, burr, mill, and/or other suitable cutter within the cut plane. The cut plane may be defined by a planar surface, slot, rail, and/or other suitable cutter guide. For example, the cutter guide may include a slot defining the cut plane. The slot may receive a saw blade and constrain the saw blade to motion within the cut plane to produce a planar surface on a bone. The position and orientation of the cut plane may be related to the knee joint in terms of six degrees of freedom including medial/lateral position, anterior/posterior position, proximal/distal position, external rotation, extension plane rotation, and varus/valgus rotation as defined in reference to FIG. 3. The resection guide may include mechanisms to adjust one or more of these degrees of freedom relative to the knee joint.

The bone resection guide may include a fixation element for attaching the bone resection guide to the bone. The fixation element may include a roughened surface, barbs, spikes, pins, and/or other fixation elements to fix the bone resection guide in position on the bone. Separate fasteners such as pins, screws, clips, clamps, and/or other fasteners may also be used to fix the bone resection guide in position. Separate fasteners may engage the bone and surfaces, grooves, slots, holes and/or other features of the bone resection guide to hold it in position. For example, the bone resection guide may include fixation holes for receiving pins to attach the bone resection guide to the bone.

The bone resection guide may include a second cut guide having a cutter guide defining a second cut plane similarly defined in terms of six degrees of freedom. The second cut guide may be mounted relative to the first cut guide to form a cut guide assembly and to position the cut planes in predetermined relationship to one another. The resection guide may include mechanisms to simultaneously adjust the position and orientation of both cut planes while keeping their relationship constant and/or to adjust the relative relationship between the first and second cut planes. The mechanisms may allow simultaneous and/or relative adjustment of any one or more of the three translational and three angular positioning parameters. For example, the resection guide may include a mechanism to simultaneously adjust all six parameters of the two cut planes and further allow relative adjustment of the extension plane rotation of the two cut planes.

The cut guide assembly may guide cutting of two different bones. For example, the first cut guide may guide a cutter to cut the tibia and the second cut guide may guide a cutter to cut the femur. For example, the cut guide assembly may be mounted to the tibia or femur and one of the cut guides positioned to guide a cutter in a desired cut plane. Where the only relative adjustment between the cut guides is relative extension plane rotation, the positioning of the first cut guide may establish the medial/lateral position, anterior/posterior position, proximal/distal position, external rotation, and varus/valgus rotation of the assembled cut planes. The other cut guide may then be adjusted relative to the first for a desired relative extension plane rotation. For example, the cut guide assembly may be mounted and adjusted to cut the femur or tibia first and allow extension plane adjustment and cutting of the other of the two bones in a linked cut arrangement. In another example, the cut guide assembly may be mounted and adjusted to cut the femur or tibia first and then readjusted relative to one or more degrees of freedom to cut the other bone in a non-linked cut arrangement. The assembly may include a mounting base fixed to the bone and to which the cut guides are mounted. The mounting base may serve as single mounting point for tibial and femoral bone cutting in linked or non-linked procedures, for operation on left and/or right sides of the knee, for unicondylar knee replacement procedures, and total condylar knee replacement procedures.

The bone resection guide may include a fixation portion for mounting the first cut guide relative to the surgical site. The fixation portion may include a hinge to allow the first cut guide to swing from a first position to a second position. For example, the fixation portion may include a mounting base for attachment to a bone and the first cut guide may be hingedly connected to the mounting base such that the first cut guide can rotate about the hinge from a position near the bone to a position spaced from the bone and back to its original position. The hinge may permit the cut guide to be temporarily rotated away from the surgical site to allow access to manipulate the joint, modify the incision, insert trial components, adjust the patient's position, and/or for any other purpose. After the purpose is accomplished, the cut guide may be rotated back precisely to its original position. In another example, the cut guide may be rotated about the hinge from a position adjacent a left side of the knee to a position adjacent the right side of the knee to permit selective operation on the left and right sides of the knee.

The mounting base may include an initial and a secondary fixation mechanism. The initial fixation mechanism may allow one or more degrees of adjustment freedom to the position of the mounting base relative to the bone. The secondary fixation mechanism may secure the mounting base in fixed relationship to the bone. The initial fixation mechanism may include a portion mounted to the bone and a portion adjustably engaging the mounting base. For example, the initial fixation system may include a bone penetrating mounting portion and an articulating end engaging the mounting to permit angular adjustment of the mounting base relative to the bone. For example, the articulating end may allow one degree of rotational freedom to allow the mounting base to be angled relative to the bone to adjust the extension plane rotation of the cut plane. The secondary fixation mechanism may then lock the mounting base position. The secondary fixation mechanism may include clamps, pins, screws, and/or other suitable fixation elements. For example, the secondary fixation mechanism may include pins inserted through fixation holes in the mounting base to pin the mounting base in fixed relationship to the bone.

Where bone attachment elements are used with the bone resection guide they may include clamps, barbs, spikes, pins, screws, rods, and/or other suitable bone attachment elements. Where translation adjustment mechanisms are specified for the bone resection guide, they may include sliding joints, slip fits, telescoping tubes, screw jacks, rack and pinion arrangements, linkages, and/or other suitable translation adjustment mechanisms. Where angular adjustment mechanisms are specified for the bone resection guide, they may include hinge joints, knuckle joints, rolling joints, ball and socket joints, journal bearings, ball bearings, roller bearings, and/or other suitable angular adjustment mechanisms.

Positioning of the bone resection guide and adjusting the cut plane location may be aided by use of a surgical navigation system including one or more tracking elements attached to the resection guide. Each tracking element is detectable electromagnetically, acoustically, optically, and/or by other suitable detection means. The tracking element may be active or passive. For example, tracking elements may include reflective spheres, light emitting diodes, gyroscopic sensors, electromagnetic emitters, electromagnetic receivers, and/or other suitable tracking elements. The tracking element (or elements) may be positioned on the bone resection guide to indicate the position of the resection guide within the surgical coordinate system. The position of the cut plane may then be resolved by the surgical navigation system from a predetermined relationship between the tracking element and the cut plane. The tracking element may be permanently mounted to the bone resection guide or be temporarily mounted for adjusting the resection guide and then being removed. The tracking element may be mounted to the cutter guide such that it is as close as possible to the cut plane to minimize manufacturing and calibration tolerance errors. For example, where the cutter guide includes a slot or surface defining the cut plane, the tracking element may be temporarily engaged with the slot or surface and used to position the cut plane. Where the bone resection guide includes multiple cut guides mounted for relative adjustment, a tracking element may be mounted to each cut guide for guiding positioning of the cut guide assembly and the relative position of the cut guides. Alternatively, one cut guide may be positioned using the surgical navigation system and the other cut guide may be positioned relative to it using mechanisms with suitable indicia to indicate the relative position of the cut guides.

Figure 4:
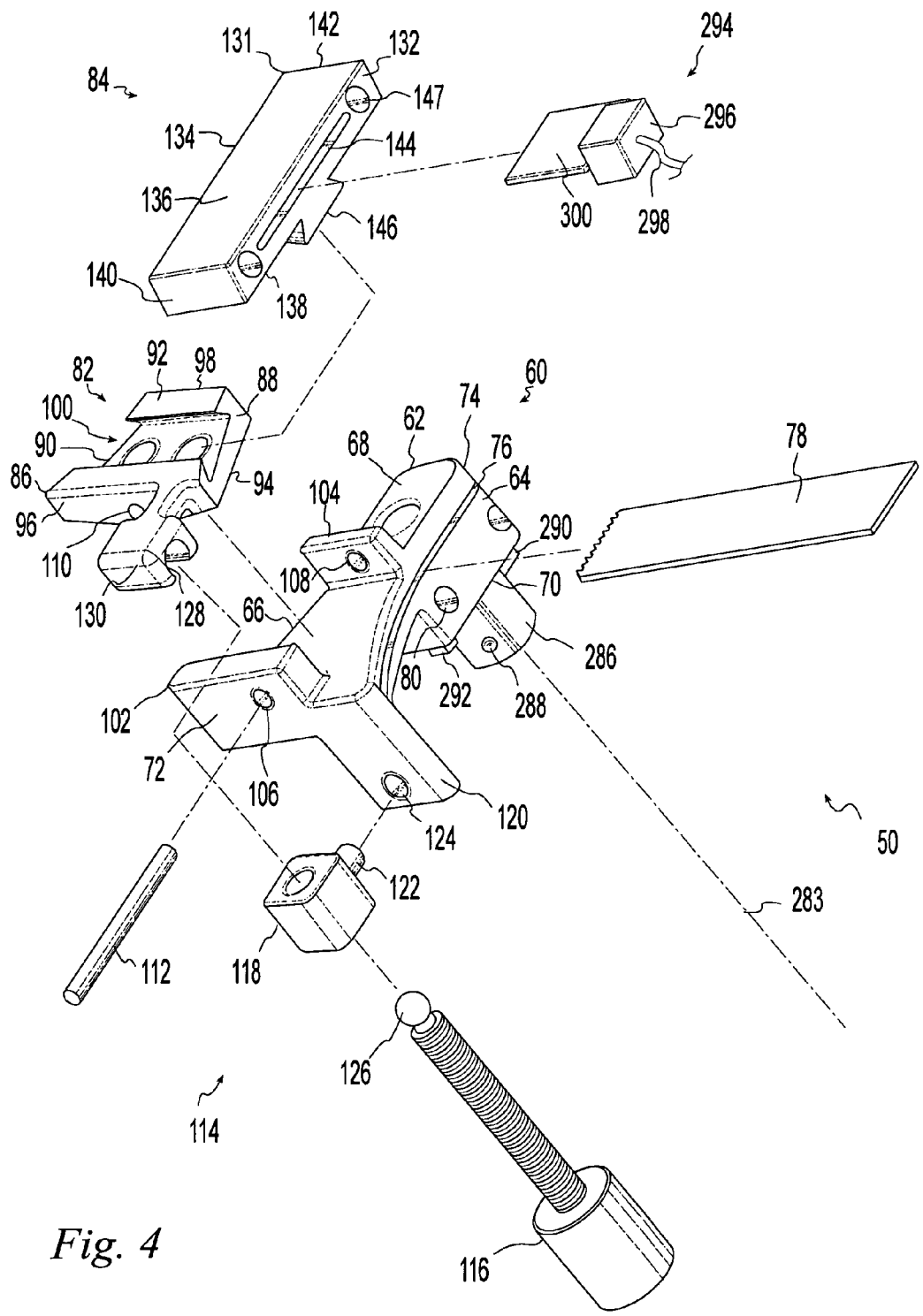
FIG. 4 is a partial exploded perspective view of a bone resection guide according to the present invention.
Figure 5:
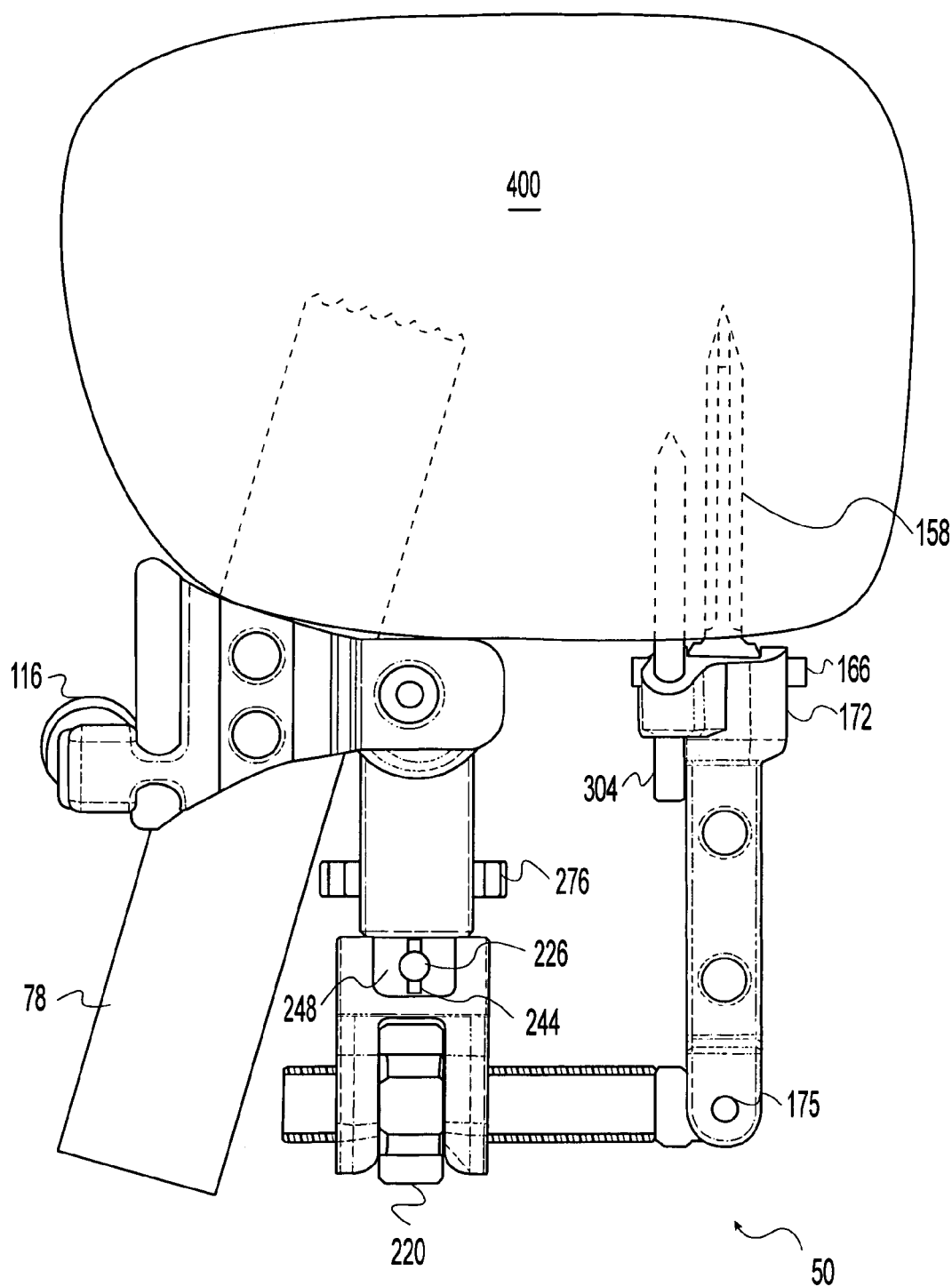
FIG. 5 is a top plan view of the resection guide of FIG. 4 mounted on a bone.
Figure 6:
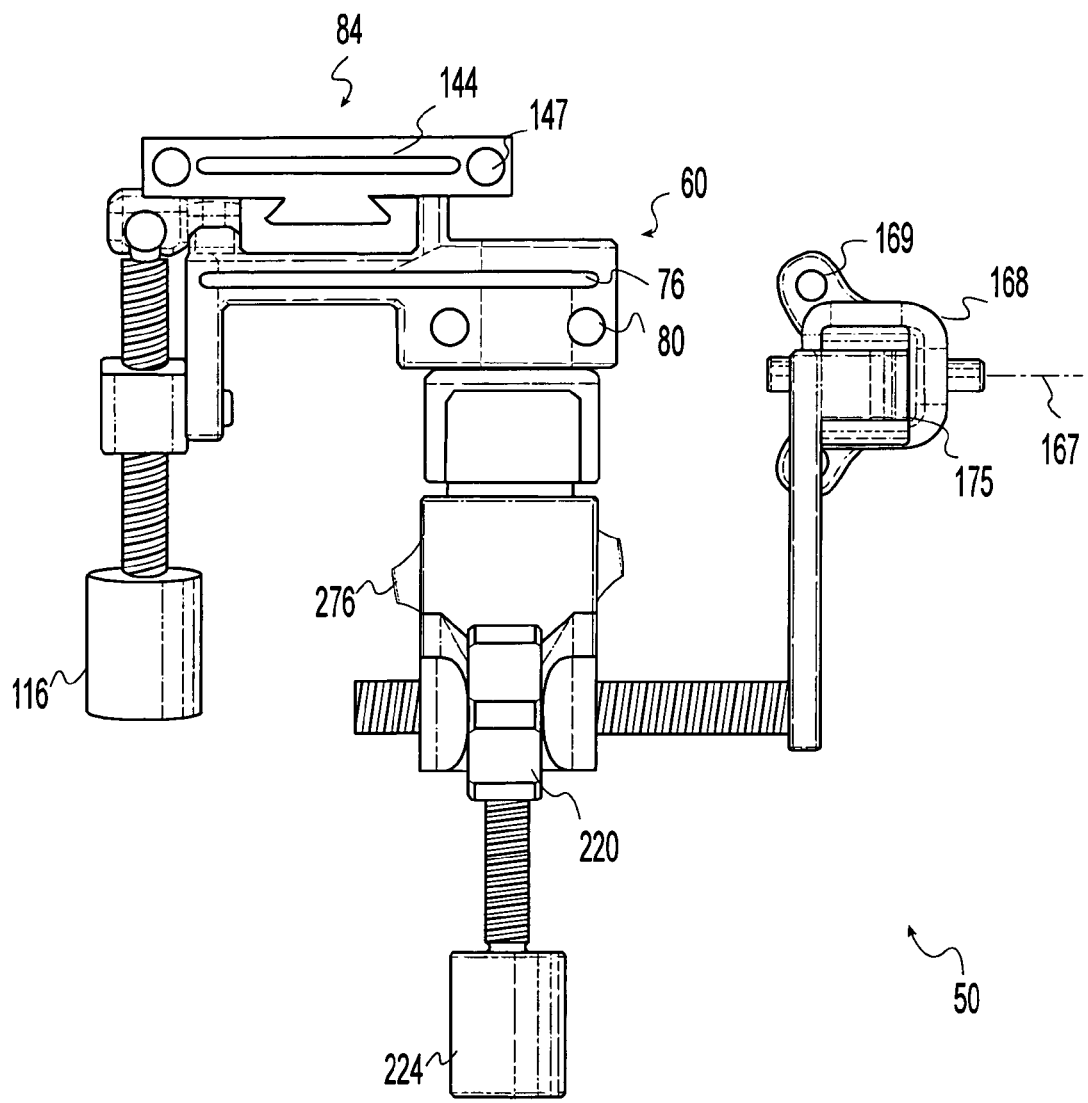
FIG. 6 is a front elevation view of the resection guide of FIG. 4.

FIGS. 4-6 show an illustrative bone resection guide 50 configured for cutting the proximal tibial surface and distal femoral surface during unicondylar knee replacement surgery. It is contemplated that the bone resection guide 50 may be adapted for total condylar knee replacement, for cutting other bone surfaces, and for other knee procedures. A tibial cut guide 60 includes a body 62 having a front 64, a back 66, a top 68, a bottom 70, and sides 72, 74 (FIG. 4). The tibial cut guide 60 includes a saw blade slot 76 extending through the body 62 from the front 64 to the back 66 and defining a cut plane. The slot 76 receives a saw blade 78 and constrains it to motion within the cut plane. The tibial cut guide 60 includes attachment holes 80 for receiving pins or screws to secure the tibial cut guide 60 in fixed relation to the tibia.

The tibial cut guide 60 further includes a femoral cut guide mounting base 82 for mounting a femoral cut guide 84 to the tibial cut guide 60. The femoral cut guide base 82 includes a body 86 having a front 88, a back 90, a top 92, a bottom 94, and sides 96, 98. A dovetail slot 100 is formed through the body 86 from the front 88 to the back 90 and opens through the top 92 of the femoral cut guide base 82. The tibial cut guide 60 includes two walls 102, 104 extending upwardly from its top 68 to define an extension plane adjustment yoke. Aligned holes 106, 108 in the walls are collinear with a side 96 to side 98 hole 110 through the femoral cut guide base 82. The femoral cut guide base 82 is mounted for rotation on the tibial cut guide 60 with a pivot pin 112 extending through the mounting holes 106, 110, 108. The bottom 94 of the femoral cut guide base 82 is adjacent the top of the tibial cut guide 60 and the femoral cut guide base 82 can pivot through a range of approximately ten degrees about the pivot pin 112. With the tibial cut guide 60 mounted on the anterior side of the tibia, the femoral cut guide base 82 pivots in extension plane rotation.

An extension plane adjustment mechanism 114 includes an extension plane adjustment screw 116 threadably engaged with a screw block 118. The screw block 118 is pivotably mounted on a wall 120 projecting downwardly from the tibial cut guide 60. A block trunnion 122 is journaled in an opening 124 to permit the screw block 118 to pivot parallel to the femoral cut guide base 82. The extension plane adjustment screw 116 includes a hemispherical ball end 126 that is received in a hemispherical seat 128 of an arm 130 extending outwardly from the side of the femoral cut guide base 82. Rotating the extension plane adjustment screw 116 to cause it travel up and down in the screw block 118 pivots the arm 130 and consequently the femoral guide base 82 about the pivot pin 112.

The femoral cut guide 84 includes a body 131 having a front 132, a back 134, a top 136, a bottom 138, and sides 140, 142. A saw guide slot 144 extends through the body 131 from the front 132 to the back 134 to define a cut plane. A dovetail slide 146 extends downwardly from the bottom 138 of the femoral cut guide 84. The dovetail slide 146 engages the dovetail slot 100 on the femoral cut guide mounting base 82 to secure the femoral cut guide 84 to the tibial cut guide 60. Attachment holes 147 extend through the body 131 from front to back for receiving pins or screws to secure the femoral cut guide 84 in fixed relation to the femur. With the femoral cut guide 84 mounted to the tibial cut guide 60, the cut planes defined by the saw slots 144, 76 are in adjustable relationship to one another. Turning the extension plane adjustment screw 116 causes the cut slots 144, 76 to move to change their relative extension plane rotation about the pivot pin 112. All other cut plane position characteristics, measured at the pivot pin 112, are held in fixed relationship when the extension plane adjustment screw 116 is rotated.

Figure 4B:
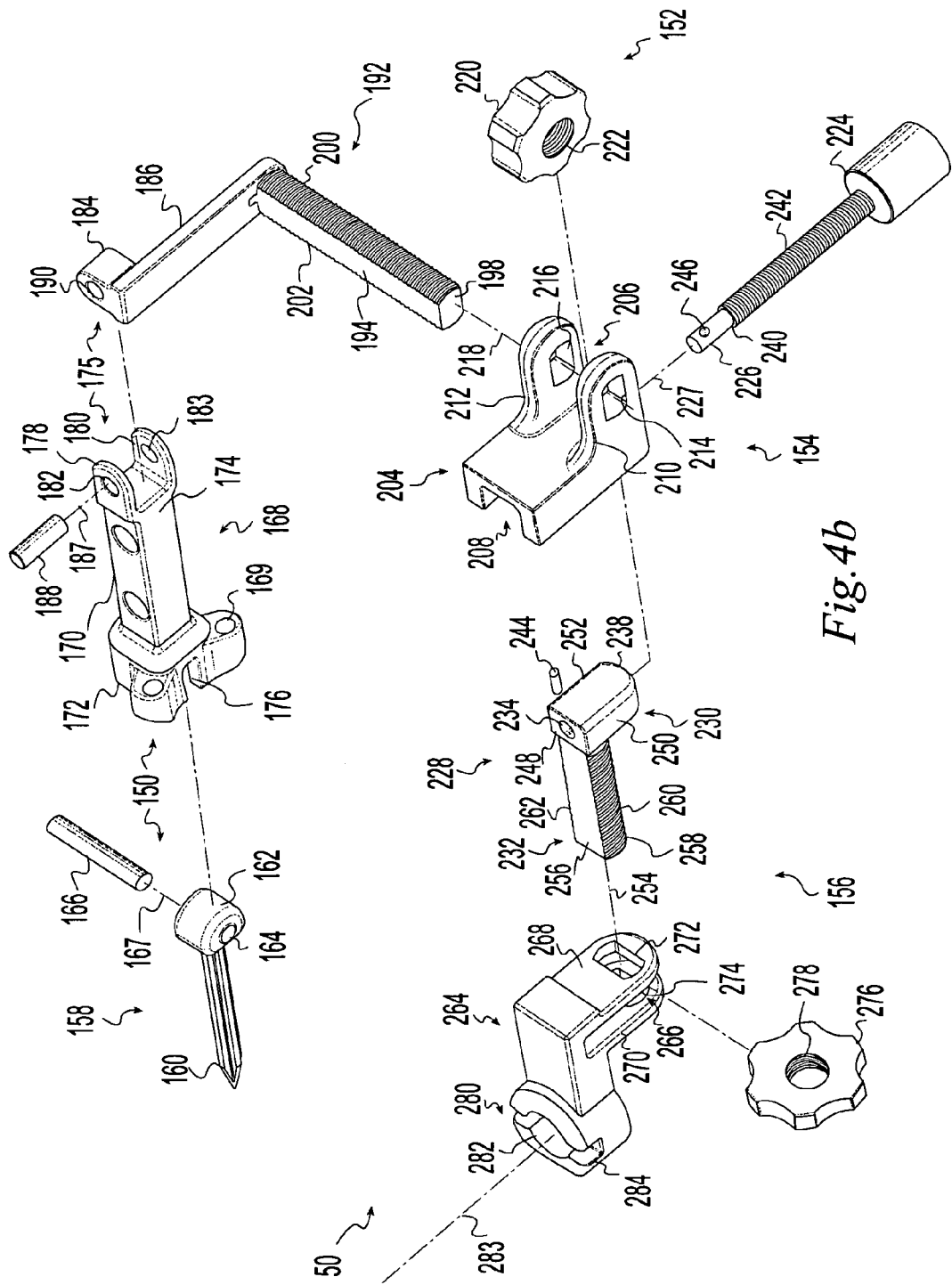
FIG. 4b is a continuation of FIG. 4.

The illustrative resection guide 50 further includes a mounting base assembly 150 a medial/lateral adjustment mechanism 152, a height adjustment mechanism 154, and an anterior/posterior adjustment mechanism 156 (FIG. 4b). The mounting base assembly 150 includes a bone spike 158 having an elongated pointed shaft 160 able to be driven into the bone. The spike 158 includes a head 162 defining an arcuate pivot surface and being intersected by a through pivot hole 164. A spike pivot pin 166 is pressed through and retained by the pivot hole 164. The spike 158 defines the mounting point for the resection guide 50 on the bone. A mounting base 168 includes an elongated body 170 having a spike receiving end 172 and a hinge end 174. The spike receiving end 172 defines an arcuate saddle (not visible) and pivot slots 176 for receiving the head 162 and pivot pin 166 of the spike in a loose press-fit for one degree of rotational freedom about the pivot pin axis 167. The mounting base 168 further includes attachment holes 169 for receiving pins or screws to secure the mounting base 168 in fixed relation to the tibia. The hinge end 174 defines a hinge 175 including a hinge yoke defined by opposing sides 178, 180 and through holes 182, 183. The yoke, receives a hinge knuckle 184 extending from a hinge link 186. The knuckle 184 is mounted within the yoke for one degree of rotational freedom about the axis 187 of a hinge pin 188 pressed through a bore 190 in the knuckle and the holes 182, 183 in the yoke. In the illustrative resection guide 50, the hinge link 186 can rotate 180 degrees about the hinge pin 188. The hinge pin axis 187 is perpendicular to the pivot pin axis 167 of the spike 158.

A medial/lateral adjustment rod 192 extends from the hinge link 186 perpendicular to the hinge pin axis 187. The medial/lateral adjustment rod 192 includes flattened top and bottom surfaces 194, 196 and threaded arcuate sides 200, 202. A two-axis translational adjustment base 204 includes a medial/lateral adjustment yoke 206 and a height adjustment slot 208. The medial/lateral adjustment yoke 206 is defined by opposing sides 210, 212 and through holes 214, 216. The holes 214, 216 have flattened tops and bottoms corresponding to the flattened top and bottom surfaces 194, 196 of the medial/lateral adjustment rod 192 such that the holes 214, 216 receive the medial/lateral adjustment rod 192 for one degree of translational freedom along the medial/lateral adjustment axis 218. A medial/lateral adjustment nut 220 includes a threaded bore 222. The medial/lateral adjustment nut 220 is mounted in the yoke 206 in threaded engagement with the medial/lateral adjustment rod 192 such that rotating the medial/lateral adjustment nut 220 translates the translational adjustment base 204 relative to the medial/lateral adjustment rod 192 along the medial/lateral adjustment axis 218.

The two-axis translational adjustment base 204 receives a height adjustment screw 224 in threaded engagement (not show) such that a smooth end 226 of the height adjustment screw 224 projects into the height adjustment slot 208 along a height adjustment axis 227 perpendicular to the medial/lateral adjustment axis 218. An anterior/posterior adjustment body 228 includes a first end defining a height adjustment boss 230 and a second end defining an anterior/posterior adjustment rod 232. The height adjustment boss 230 includes a through bore 234 engaged with the smooth end 226 of the height adjustment screw 224 for one degree of rotational freedom about the height adjustment axis 227. The bore 234 is stepped to form an internal shoulder (not shown) facing the bottom 238 of the height adjustment boss 230. The internal shoulder of the bore 234 rests on a shoulder 240 formed on the height adjustment screw 224 between the smooth end 226 and the threaded portion 242. A retention pin 244 extends through a hole 246 in the smooth end 226 of the height adjustment screw and abuts the top 248 of the height adjustment boss 230 such that the height adjustment boss 230 is longitudinally trapped on the smooth end 226 of the height adjustment screw 224 for relative rotation. The height adjustment boss 230 is received in the height adjustment slot 208 for translation of the boss 230 within the slot 208 along the height adjustment axis 227. The sides 250, 252 of the height adjustment boss 230 define a close slip fit within the slot 208.

The anterior/posterior adjustment rod 232 extends from the height adjustment boss 230 along an anterior/posterior adjustment axis 254 perpendicular to the height adjustment axis 227. The anterior/posterior adjustment rod 232 includes flattened top and bottom surfaces 256, 258 and threaded arcuate sides 260, 262. An anterior/posterior adjustment base 264 includes an anterior/posterior adjustment yoke 266 defined by opposing sides 268, 270 and through holes 272, 274. The holes 272, 274 have flattened tops and bottoms corresponding to the flattened top and bottom surfaces 256, 258 of the anterior/posterior adjustment rod 232 such that the holes 272, 274 receive the anterior/posterior adjustment rod 232 for one degree of translational freedom along the anterior/posterior adjustment axis 254. An anterior/posterior adjustment nut 276 includes a threaded bore 278. The anterior/posterior adjustment nut 276 is mounted in the yoke 266 in threaded engagement with the anterior/posterior adjustment rod 232 such that rotating the anterior/posterior adjustment nut 276 translates the anterior/posterior adjustment base 264 relative to the anterior/posterior adjustment rod 232 along the anterior/posterior adjustment axis 254.

The anterior/posterior adjustment base 264 includes a tibial cut guide 60 mounting portion 280 including a bore 282 having a longitudinal bore axis 283 perpendicular to the anterior/posterior adjustment axis 254 and a pair of opposed antirotation slots 284. The tibial cut guide 60 includes a cylindrical spigot 286 extending downwardly from the bottom 70 and receivable in the bore 282. The spigot 286 includes a spring loaded ball plunger 288 that snaps into a groove (not visible) in the bore 282 to releasably retain the spigot 286 axially within the bore. A pair of lugs 290, 292 projects downwardly from the bottom 70 of the tibial cut guide 60 adjacent to the spigot 286 to engage the antirotation slots 284 to fix the rotational position of the tibial cut guide 60 relative to the anterior/posterior adjustment base 264. The tibial cut guide 60 may be engaged with the anterior/posterior adjustment base 264 in either of two rotational positions 180 degrees apart.

A tracking element may be provided to enable use of the bone resection guide 50 with a surgical navigation system. The tracking element may be permanently or removably mounted anywhere on the resection guide 50. However, to reduce positioning errors and simplify use, it is preferable to mount the tracking element as close as possible to the cut slots 76, 144. For example, the tracking element may be embedded within or attached to the tibial cut guide body 62 and/or the femoral cut guide body 131. In the illustrative apparatus, a tracking assembly 294 (FIG. 4) comprises a housing 296 containing one or more tracking elements such as electromagnetic coils. A cable 298 connects the tracking assembly 294 to the surgical navigation system. A plate 300 extends from the housing 296 to engage the saw slots 144, 76 in slip fit relationship.

The bone resection guide 50 may be used in a variety of ways to resect one or more bones. For example the tibial cut guide 60 may be positioned adjacent to a tibia and the cut plane of the saw slot 76 adjusted to a desired position. Fasteners are inserted through attachment holes 80 to secure the tibial cut guide 60. A saw blade is guided by the saw slot 76 to cut the tibia in the cut plane. The positioning of the tibial cut guide 60 may be aided by engaging the tracking assembly 294 with the saw slot 76 and using a surgical navigation system to guide positioning of the cut plane. The femoral cut guide 84 may be mounted on the tibial cut guide 60 to provide linked cuts of the tibia and femur. Either of the tibia and femur may be cut first. For example, the tibial cut guide may be positioned and mounted to cut the tibia first. This sets the medial/lateral position, anterior/posterior position, proximal/distal position, external rotation, extension plane rotation, and varus/valgus rotation of the tibial cut plane. Rotating the extension plane adjustment screw 116 sets the extension plane rotation angle of the femoral cut guide 84 while keeping all other relative cut plane position characteristics, measured at the pivot pin 112, in fixed relationship. The femoral cut plane extension plane angle may be set by measuring the relative angle between the tibial and femoral cut guides with a protractor, reading angle indicia formed on the resection guide 50 to indicate the relative angle, and/or engaging the navigation tracking assembly 294 with the femoral saw slot 144 and using the surgical navigation system. Once the femoral extension plane angle has been set, the femoral cut guide may be secured to the femur by inserting fasteners through the attachment holes 147. In another exemplary procedure, the femoral cut guide 84 may be positioned first and then the tibial cut guide 60 extension plane angle set.

Figure 1:
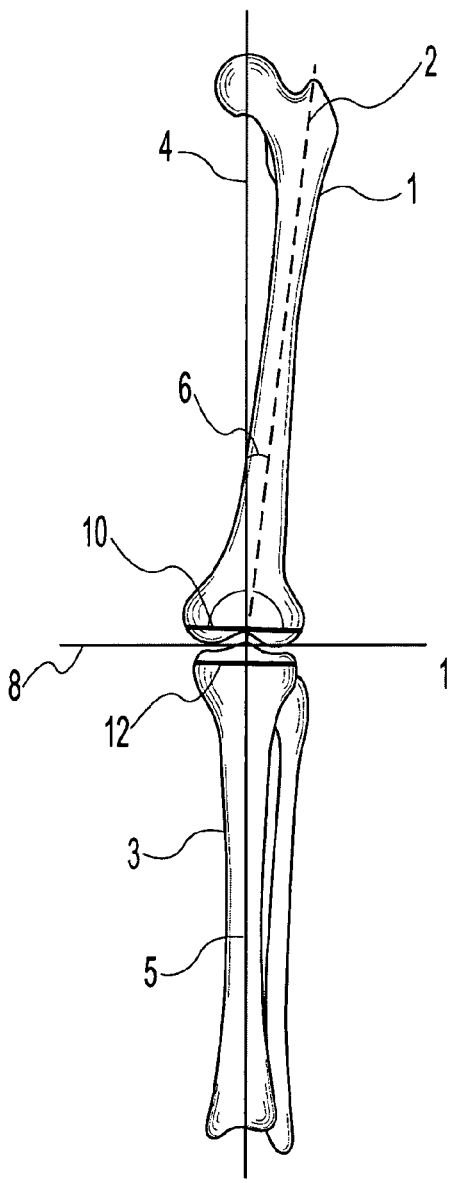
FIG. 1 is a front elevation view of a tibia and a femur showing axes of the knee joint.
Figure 2:
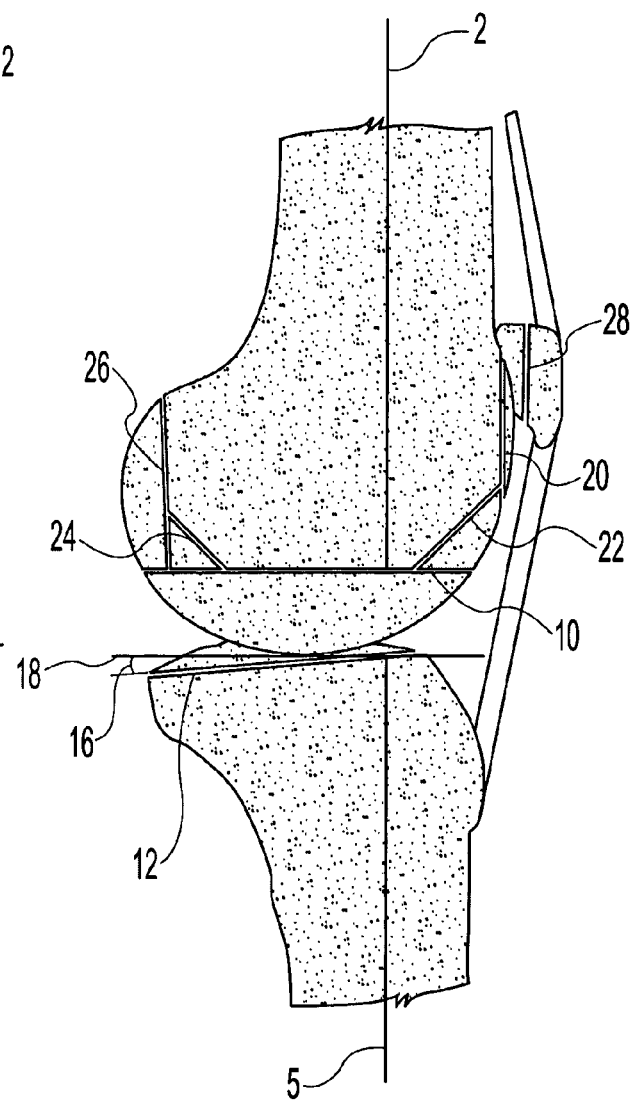
FIG. 2 is a side section view of a knee joint showing typical bone cuts used in replacing the joint surfaces.

The entire bone resection guide 50 shown in FIG. 1 may be assembled to simplify adjustment of the cut guide positions. Rotation of the mounting base 168 about the pin axis 167 to adjust extension plane angle, rotation of medial/lateral adjustment nut 220, rotation of height adjustment screw 224, and rotation of anterior/posterior adjustment nut 276 all simultaneously affect the position of the tibial and femoral cut guides 60, 84 while their relative position remains constant. Rotation of the extension plane adjustment screw 116 further allows adjustment of the extension plane angles of the tibial and femoral guides 60, 84 relative to one another. For example, the bone spike 158 may be driven into a bone adjacent to the knee joint to provide a secure mounting point. In the illustrative example, the bone spike 158 is driven into the tibia 400 (FIG. 5). The remaining pieces of the bone resection guide 50 are mounted on the bone spike 158 by pressing the spike receiving end 172 of the mounting base 168 over the head 162 of the bone spike 158. The bone resection guide 50 is pivoted up and down about the spike pivot pin 166 to adjust the extension plane angle of one of the cut guides 60, 84. For example, if the tibial cut plane is being used as the initial reference plane, the bone resection guide 50 is pivoted to set the tibial plane extension plane angle. Pins 304 are driven through the attachment holes to fix the extension plane angle and secure the mounting base 168 to the tibia.

The hinge 175 allows the resection guide 50 to be swung away from the knee joint to provide better access if needed during the procedure. The resection guide 50 may then be swung back to its original position. The hinge 175 also allows the resection guide 50 to be swung between left and right positions to permit positioning the cut guides 60, 84 adjacent the left or right side of the knee. The medial/lateral adjustment nut 220, height adjustment screw 224, and anterior/posterior adjustment nut 276 are rotated to bring the cut plane into the desired position. The relative extension plane angle may be adjusted using the extension plane adjustment screw 116 as previously described. The surgical navigation system may be used to guide any of these adjustments and the resection guide 50 provides a solid base for fine adjustments using the surgical navigation system. Two cut guides have been shown to allow a linked cut surgical procedure. However, a single cut guide may be used to cut both the femur and the tibia in an unlinked surgical procedure by first cutting one bone, repositioning the guide, and then cutting the other bone.

Although examples of a bone resection guide and its use have been described and illustrated in detail, it is to be understood that the same is intended by way of illustration and example only and is not to be taken by way of limitation. The invention has been illustrated in use to cut the proximal tibia and distal femur to prepare them for receiving knee implant components during knee replacement surgery. However, the bone resection guide may be configured to guide other bone cuts for unicondylar as well as total condylar knee replacement procedures. Accordingly, variations in and modifications to the bone resection guide and its use will be apparent to those of ordinary skill in the art, and the following claims are intended to cover all such modifications and equivalents.

What is claimed is:

1. An apparatus for guiding a bone cut during knee joint replacement surgery, the knee joint comprising a tibia and a femur and having a medial/lateral axis, an anterior/posterior axis, and a proximal/distal axis, rotation about the medial/lateral axis corresponding to extension plane rotation, and rotation about the anterior/posterior axis corresponding to varus/valgus rotation, the apparatus comprising:

a first cut guide defining a first cut plane characterized by an angle relative to the knee joint;

a second cut guide defining a second cut plane characterized by an angle relative to the knee joint, the second cut guide being mounted to the first cut guide; and a relative angle adjustment mechanism operably connected between the first and second cut guides to adjust the relative angle between the cut planes of the first and second cut guides;

wherein the first cut guide comprises a tibial cut guide and the second cut guide comprises a femoral cut guide, the femoral cut guide being pivotably mounted to the tibial cut guide, the angle adjustment mechanism being operable to pivot the femoral cut guide relative to the tibial cut guide to adjust the relative extension plane angle between the two cut planes.

2. The apparatus of claim 1 wherein the tibial cut guide and femoral cut guide comprise a cut guide assembly, the apparatus further comprising a simultaneous adjustment mechanism operably connected to the cut guide assembly and being connectable to the bone, the simultaneous adjustment mechanism being operable to translate the cut guide assembly relative to the knee joint.

3. The apparatus of claim 2 wherein the simultaneous adjustment mechanism is operable to translate the cut guide assembly parallel to the medial/lateral axis, to translate the cut guide assembly parallel to the proximal/distal axis, and to translate the cut guide assembly parallel to the anterior/posterior axis.

4. The apparatus of claim 2 wherein the simultaneous adjustment mechanism is further operable to adjust the extension plane rotation of the cut guide assembly relative to the knee joint.

5. The apparatus of claim 1 further comprising a surgical navigation system tracking element connectable to one of the first and second cut guides to guide positioning of the apparatus.

6. The apparatus of claim 5 wherein the tracking element is alternatively connectable to the first and second cut guides to allow selective navigation of the cut guides relative to one another and simultaneous navigation of the cut guides together.

7. An apparatus for guiding a bone cut during knee joint replacement surgery, the knee joint comprising a tibia and a femur and having a medial/lateral axis, an anterior/posterior axis, and a proximal/distal axis, rotation about the medial/lateral axis corresponding to extension plane rotation, and rotation about the anterior/posterior axis corresponding to varus/valgus rotation, the apparatus comprising:
- a mounting base connectable to the bone in fixed relationship to the bone;
- a first cut guide defining a first cut plane, the first cut guide being hinged to the mounting base the first cut guide being rotatable about the hinge between a first position in which the first cut guide is adjacent to the bone and a second position in which the first cut guide is spaced from the bone; and
- an adjustment mechanism operably connected between the hinge and the first cut guide, the adjustment mechanism being operable to translate the first cut guide relative to the hinge, wherein the adjustment mechanism is operable to independently translate the first cut guide parallel to the medial/lateral axis, translate the first cut guide parallel to the proximal/distal axis, and translate the first cut guide parallel to the anterior/posterior axis relative to the hinge.

8. An apparatus for guiding a bone cut during knee joint replacement surgery, the knee joint comprising a tibia and a femur and having a medial/lateral axis, an anterior/posterior axis, and a proximal/distal axis, rotation about the medial/lateral axis corresponding to extension plane rotation, and rotation about the anterior/posterior axis corresponding to varus/valgus rotation, the apparatus comprising:
- a mounting base connectable to the bone in fixed relationship to the bone;
- a first cut guide defining a first cut plane, the first cut guide being hinged to the mounting base the first cut guide being rotatable about the hinge between a first position in which the first cut guide is adjacent to the bone and a second position in which the first cut guide is spaced from the bone;
- an adjustment mechanism operably connected between the hinge and the first cut guide, the adjustment mechanism being operable to translate the first cut guide relative to the hinge;
- a second cut guide defining a second cut plane, the second cut guide being mounted to the first cut guide; and
- a relative angle adjustment mechanism operably connected to the first and second cut guides to adjust a relative angle between the first and second cut planes.

9. The apparatus of claim 8 wherein the first position corresponds to the medial side of the knee joint and the first cut guide is further rotatable about the hinge to a third position in which the first cut guide is adjacent to the lateral side of the knee joint.

10. The apparatus of claim 8 further comprising a surgical navigation system tracking element to guide positioning of the apparatus.

11. An apparatus for guiding a bone cut during knee joint replacement surgery, the knee joint comprising a tibia and a femur and having a medial/lateral axis, an anterior/posterior axis, and a proximal/distal axis, rotation about the medial/lateral axis corresponding to extension plane rotation, and rotation about the anterior/posterior axis corresponding to varus/valgus rotation, the apparatus comprising:
- a mounting base connectable to a bone, the mounting base including an initial fixation mechanism and a secondary fixation mechanism, the initial fixation mechanism comprising a bone spike penetrably mountable to a bone in fixed relationship, the bone spike having an articulating end engageable with the mounting base for rotation about an axis, the secondary fixation mechanism comprising a pin receiving opening in the mounting base and a pin extendable through the opening to pin the base to the bone in fixed relationship; and
- a first cut guide defining a first cut plane characterized by an extension plane angle relative to the knee joint, the cut guide being mounted to the mounting base, the initial fixation mechanism of the mounting base being operable to rotate the mounting base relative to the bone about an axis substantially parallel to the medial/lateral axis to vary the extension plane angle of the cut plane, the secondary fixation mechanism being operable to secure the mounting base in fixed relationship to the bone to fix the extension plane angle.

12. The apparatus of claim 11 further comprising an adjustment mechanism operably connected between the mounting base and the first cut guide, the adjustment mechanism being operable to translate the first cut guide relative to the mounting base.

13. The apparatus of claim 12 wherein the adjustment mechanism is operable to independently translate the cut guide parallel to the medial/lateral axis, translate the cut guide parallel to the proximal/distal axis, and translate the cut guide parallel to the anterior/posterior axis relative to the mounting base.

14. apparatus of claim 12 wherein the adjustment mechanism further comprises a hinge operably mounted between the first cut guide and the mounting base, the first cut guide being rotatable about the hinge between a first position in which the cut guide is adjacent to the bone and a second position in which the first cut guide is spaced from the bone.

15. The apparatus of claim 11 further comprising:
- a second cut guide defining a second cut plane, the second cut guide being mounted to the first cut guide; and
- a relative angle adjustment mechanism operably connected to the first and second cut guides to adjust a relative angle between the first and second cut planes.

16. The apparatus of claim 11 further comprising a surgical navigation system tracking element to guide positioning of the apparatus.

* * * * *